US00PP27358P2

(12) United States Plant Patent
Danziger

(10) Patent No.: US PP27,358 P2
(45) Date of Patent: Nov. 8, 2016

(54) ***CALIBRACHOA* PLANT NAMED 'DANOASNOW'**

(50) Latin Name: ***Calibrachoa* sp.**
Varietal Denomination: DANOASNOW

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 14/545,467

(22) Filed: May 7, 2015

(51) Int. Cl.
*A01H 5/02* (2006.01)

(52) U.S. Cl.
USPC ..... Plt./413

(58) Field of Classification Search
USPC ..... Plt./413
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Calibrachoa* cultivar named 'DANOASNOW' is disclosed, characterized by a mounded growth habit, very well branched plant form, and an abundance of large creamy white flowers with light yellow centers. The new variety is tolerant of high temperatures above 28° C. The new variety is a *Calibrachoa*, normally produced as an outdoor garden or container plant.

2 Drawing Sheets

Figure 1:
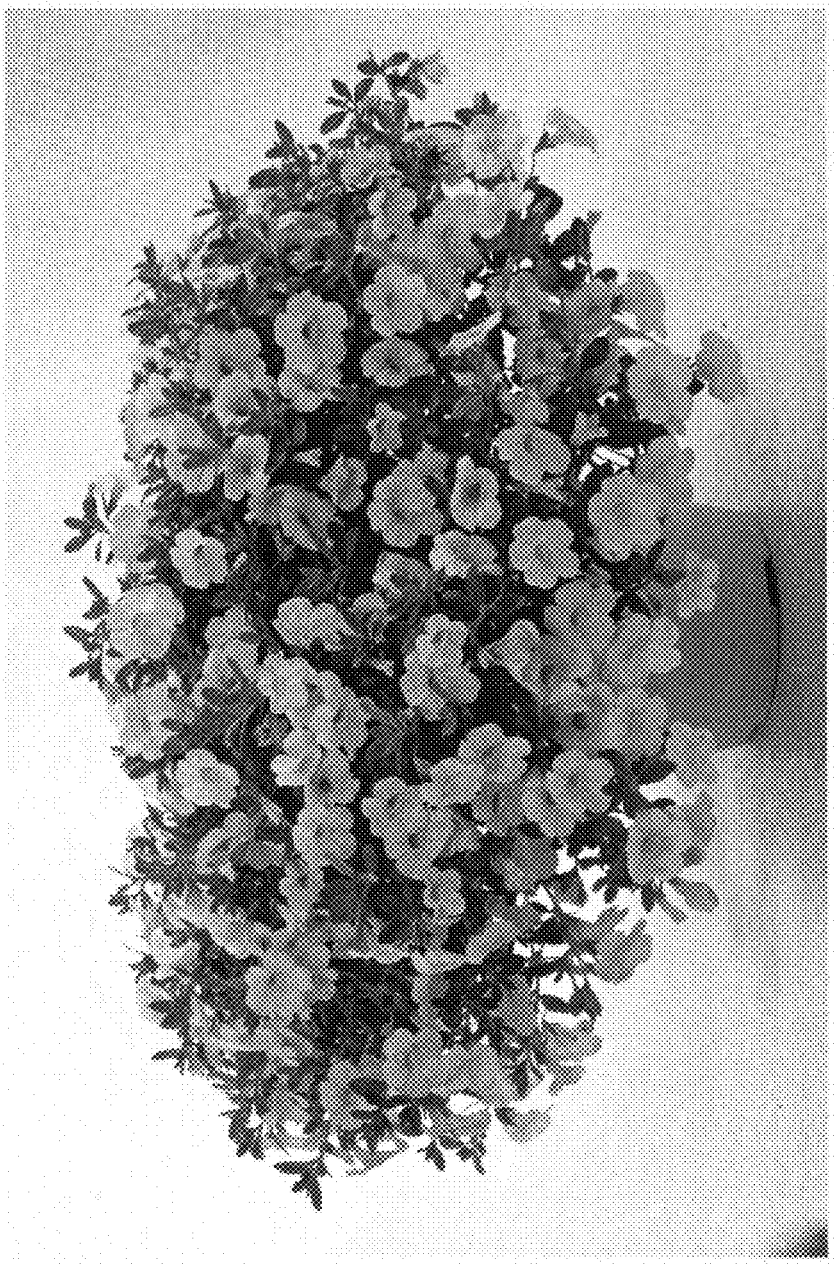

Latin name of the genus and species: *Calibrachoa* sp.
Variety denomination: 'DANOASNOW'.

BACKGROUND OF THE INVENTION

The new *Calibrachoa* cultivar is a product of a planned breeding program conducted by the inventor, Gavriel Danziger, in Moshav Mishmar Hashiva, Israel. The objective of the breeding program was to produce new *Calibrachoa* varieties for ornamental commercial applications. The cross resulting in this new variety was made during December of 2011.

The seed parent is the, unpatented, proprietary variety referred to as *Calibrachoa* 'cv.5-349'. The pollen parent is the unpatented, propriety variety referred to as *Calibrachoa* 'cv. 11-2621'. The new variety was discovered in July of 2012 by the inventor in a group of seedlings resulting from the 2011 crossing, in a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel in July of 2012 and has shown that the unique features of this cultivar are stable and reproduced true to type in more than 20 successive generations.

SUMMARY OF THE INVENTION

The cultivar 'DANOASNOW' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOASNOW' These characteristics in combination distinguish 'DANOASNOW' as a new and distinct *Calibrachoa* cultivar:

1. Very well branched plant.
2. Mounded growth habit.
3. Large flower size.
4. Abundant flowering.
5. Flower color is creamy white with a light yellow center.

Plants of the new cultivar 'DANOASNOW' are similar to plants of the seed parent, *Calibrachoa* 'cv. 5-349' in most horticultural characteristics, however, plants of the new cultivar 'DANOASNOW' differ in the following;

1. Mounded growth habit, the seed parent has a trailing growth habit.
2. Larger flower size than the seed parent.
3. Flowers are creamy white with a yellow center, whereas the seed parent has solid creamy white colored flowers.
4. More flowers than the seed parent.
5. More branches than the seed parent.

Plants of the new cultivar 'DANOASNOW' are similar to plants of the pollen parent, *Calibrachoa* 'cv. 11-2621' in most horticultural characteristics, however, plants of the new cultivar 'DANOASNOW' differ in the following;

1. Mounded growth habit, the pollen parent has a semi-trailing growth habit.
2. Larger flower size than the pollen parent.
3. Flowers are creamy white with a yellow center, whereas the pollen parent has solid pure white colored flowers.
4. More flowers than the pollen parent.
5. More branches than the pollen parent.

COMMERCIAL COMPARISON

Plants of the new cultivar 'DANOASNOW' are comparable to the unpatented commercial variety *Calibrachoa* 'DANOA32'. The two *Calibrachoa* varieties are similar in most horticultural characteristics; however, the new variety 'DANOASNOW' differs in the following:

1. More branches per plant than this comparator.
2. Mounded growth habit. The comparator's growth habit is trailing.
3. Flowers are creamy white with a yellow center, whereas the comparator has solid pure white colored flowers.
4. More flowers than the comparator.
5. Later flowering than the comparator.

Plants of the new cultivar 'DANOASNOW' can also be compared to the patented commercial variety *Calibrachoa* 'DANOA53' U.S. Plant Pat. No. 22,056. The two *Calibrachoa* varieties are similar in most horticultural characteristics; however, the new variety 'DANOASNOW' differs in the following:

1. More branches per plant than the comparator.
2. Mounded growth habit. The comparator's growth habit is semi-trailing.
3. Flowers are creamy white with a yellow center, whereas the comparator has light pink flowers with dark pink centers.
4. Less plant vigor than the comparator.

BRIEF DESCRIPTION OF THE PHOTOGRAPHS

The accompanying photograph in FIG. 1 illustrates in full color a typical plant of 'DANOASNOW' grown in a nursery, in a 13 cm pot. Age of the plant photographed is approximately 60 days from a rooted cutting.

Figure 2:
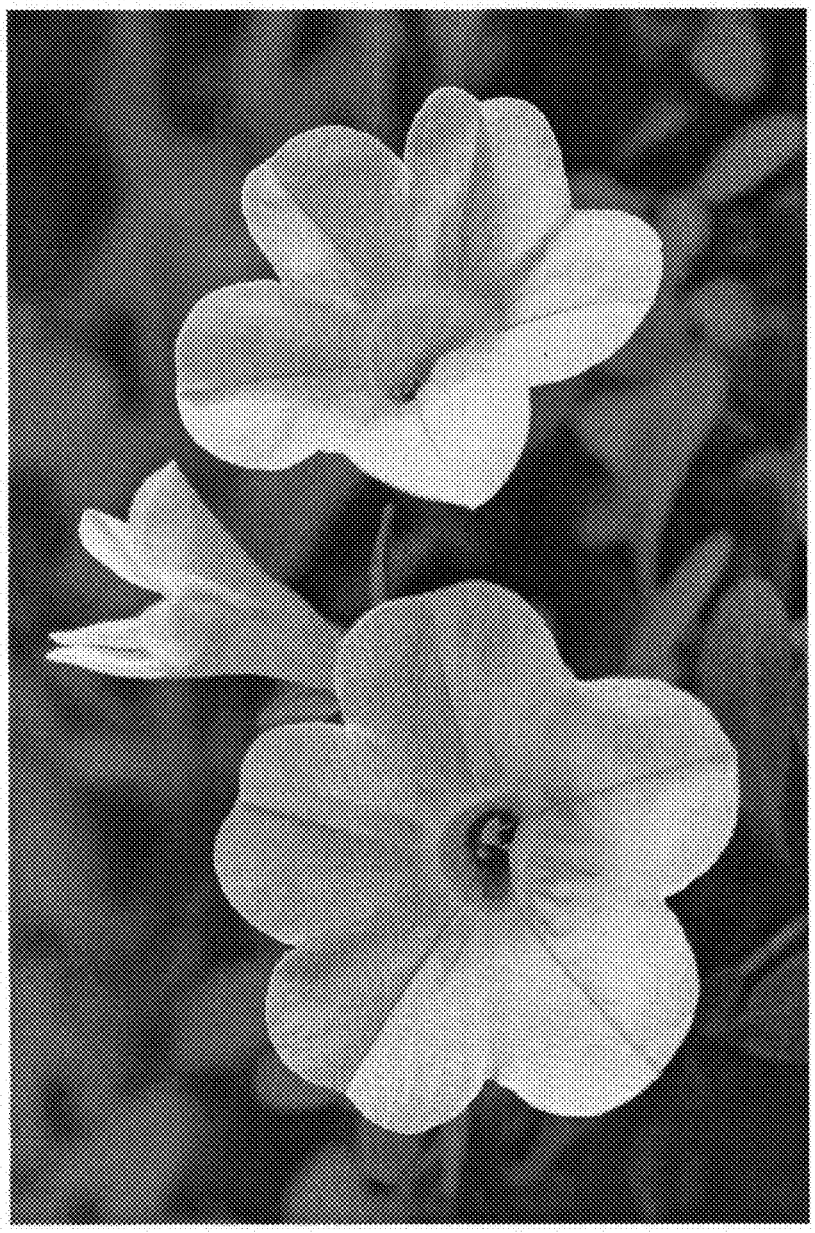

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DANOASNOW' plants grown outdoors and in greenhouse during the Spring, Summer and Autumn, in Moshav Mishmar Hashiva, Israel. The growing temperature ranged from 18° C. to 35° C. during the day and from 15° C. to 25° C. during the night. General light conditions are bright, normal sunlight. Measurements and numerical values represent averages of typical plant types.

Botanical classification: *Calibrachoa* 'DANOASNOW'.

PROPAGATION

Type of propagation typically used: Vegetative terminal cutting.
Time to initiate roots: 10-14 days.
Root description: Fibrous.

PLANT

Age of plant described: Approximately 60 days from a rooted cutting.
Pot size of plant described: 13 cm.
Growth habit: Mounded.
Height: Approximately 15 cm.
Plant spread: About 50 cm.
Growth rate: Moderate.
Branching characteristics: Very well branched.
Characteristics of primary lateral branches:
- *Quantity of primary lateral branches.*—8.
- *Length of primary lateral branches.*—About 25 cm.
- *Form.*—Cylindrical.
- *Diameter.*—0.2 cm.
- *Color.*—RHS Yellow-Green N144 D.
- *Texture.*—Slightly pubescent.
- *Strength.*—Strong and flexible.

Internode length: 2 cm.

FOLIAGE

Leaf:
- *Arrangement.*—Opposite.
- *Quantity.*—Approximately 80 per branch.
- *Average length.*—3.0 cm.
- *Average width.*—1.0 cm.
- *Shape of blade.*—Elliptic.
- *Apex.*—Rounded.
- *Base.*—Acute.
- *Margin.*—Entire.
- *Texture of top surface.*—Velvety.
- *Texture of bottom surface.*—Velvety.
- *Pubescence.*—Pubescent.
- *Aspect.*—90 degrees.
- *Color.*—Young foliage upper side: RHS Yellow-Green 146 A. Young foliage under side: RHS Yellow-Green 146 B. Mature foliage upper side: RHS Yellow-Green 147 A. Mature foliage under side: RHS Yellow-Green 147 B.
- *Venation.*—Type: Pinnate. Venation color upper side: RHS Yellow-Green 147 B. Venation color under side: RHS Yellow-Green 147 C.
- *Petiole.*—Length: 0.5 cm. Diameter: 0.2 cm. Color: RHS Yellow-Green 147 B. Texture: Velvety.

FLOWER

Natural flowering season: Spring, Summer, and Autumn in Israel.
Days to flowering from rooted cutting: About 40 days.
Inflorescence and flower type and habit: Axillary, single flower, salverform shape.
Rate of flower opening: 3 to 4 days from bud to fully opened flower.
Flower longevity on plant: 4 to 7 days.
Approximate quantity of flowers per plant: About 100.
Persistent or self-cleaning: Self-cleaning.
Bud:
- *Shape.*—Tubular.
- *Length.*—2.7 cm.
- *Diameter.*—0.7 cm.
- *Color.*—RHS Greyed-Yellow 160 C.

Flower size:
- *Diameter.*—About 4.0 cm.
- *Length.*—About 3.0 cm.
- *Flower tube diameter at distal end.*—About 1.0 cm.
- *Flower tube diameter at proximal end.*—About 0.3 cm.

Petals:
- *Length from throat.*—About 1.6 cm.
- *Width.*—About 1.5 cm.
- *Quantity.*—5.
- *Texture.*—Velvety all surfaces.

*Apex*.—Rounded.
*Margin*.—Entire.

Color:
*When opening*.—Upper surface RHS Greyed-Yellow 160 C. Lower surface: RHS Greyed-Yellow 160 C.
*Fully opened*.—Upper surface: RHS White 155 C. Lower surface: RHS White 155 C. Flower throat (inside): RHS Greyed-Yellow 160 A. Flower throat, vein: RHS Greyed-Yellow 162 C. Flower tube (outside): RHS Greyed-Yellow 160 B. Flower tube, vein: RHS Greyed-Yellow 160 A. Petal color, fading to: RHS Greyed-Yellow 160 D.

Calyx/sepals:
*Quantity per flower*.—5.
*Shape*.—Linear.
*Length*.—About 1.8 cm.
*Width*.—About 0.4 cm.
*Apex*.—Rounded.
*Base*.—Fused.
*Margin*.—Entire.
*Texture*.—Velvety.
*Color*.—Upper Surface: RHS Yellow-Green 147 A. Lower Surface: RHS Yellow-Green 147 B.

Peduncle: Not present.

Pedicel:
*Length*.—About 2 cm.
*Diameter*.—About 0.1 cm.
*Color*.—RHS Yellow-Green N144 D.
*Orientation*.—45 degrees.

Fragrance: None.

REPRODUCTIVE ORGANS

Stamens:
*Number (per flower)*.—5.
*Filament length*.—About 1 cm.
*Anthers*.—Shape: Rounded. Length: about 0.1 cm. Color: RHS Yellow 7 B.

Pollen:
*Color*.—RHS Yellow 7 C.
*Amount*.—Moderate.

Pistils:
*Quantity per flower*.—1.
*Length*.—About 1.4 cm.
*Styles*.—Length: about 1.0 cm. Color: RHS Green-Yellow 1 B. Stigma: Shape: Rounded. Color: RHS Yellow-green N144 B. Ovary Color: RHS Yellow-Green 149 C.

OTHER CHARACTERISTICS

Seeds and fruits: About 30 brown, rounded seeds of about 0.5 mm diameter, per one brown, conical capsule. Minute, not accurately measured with R.H.S. chart.

Disease/pest resistance: Neither resistance nor susceptibility to normal diseases and pests of *Calibrachoa* have been observed.

Temperature tolerance: 5° to 30° C.

What is claimed is:

1. A new and distinct cultivar of *Calibrachoa* plant named 'DANOASNOW' as herein illustrated and described.

* * * * *